United States Patent [19]
Nara et al.

[11] 3,939,043
[45] Feb. 17, 1976

[54] ANTIBIOTICS DESIGNATED XK-88 SERIES AND PROCESS FOR PRODUCTION THEREOF

[75] Inventors: Takashi Nara, Tokyo; Seigo Takasawa, Hadano; Ryo Okachi, Machida; Isao Kawamoto, Machida; Mitsuyoshi Yamamoto, Machida; Seiji Sato, Machida; Tomoyasu Sato, Machida; Atsuko Morikawa, Tama, all of Japan

[73] Assignee: Abbott Laboratories, North Chicago, Ill.

[22] Filed: Oct. 21, 1974

[21] Appl. No.: 516,816

[30] Foreign Application Priority Data
Oct. 24, 1973 Japan............................ 48-118932

[52] U.S. Cl............................ 195/80 R; 260/345.9
[51] Int. Cl.² .......................................... C12D 9/00
[58] Field of Search ................................. 195/80 R

[56] References Cited
UNITED STATES PATENTS
3,652,536   3/1972   Sebek et al. ..................... 195/80 R Primary Examiner—A. Louis Monacell
Assistant Examiner—Robert J. Warden
Attorney, Agent, or Firm—Fitzpatrick, Cella, Harper & Scinto

[57] ABSTRACT

A novel series of antibiotics designated the XK-88 series are produced by culturing a microorganism belonging to the genus Streptomyces in a nutrient medium and thereafter recovering the antibiotics from the culture liquor.

7 Claims, 15 Drawing Figures

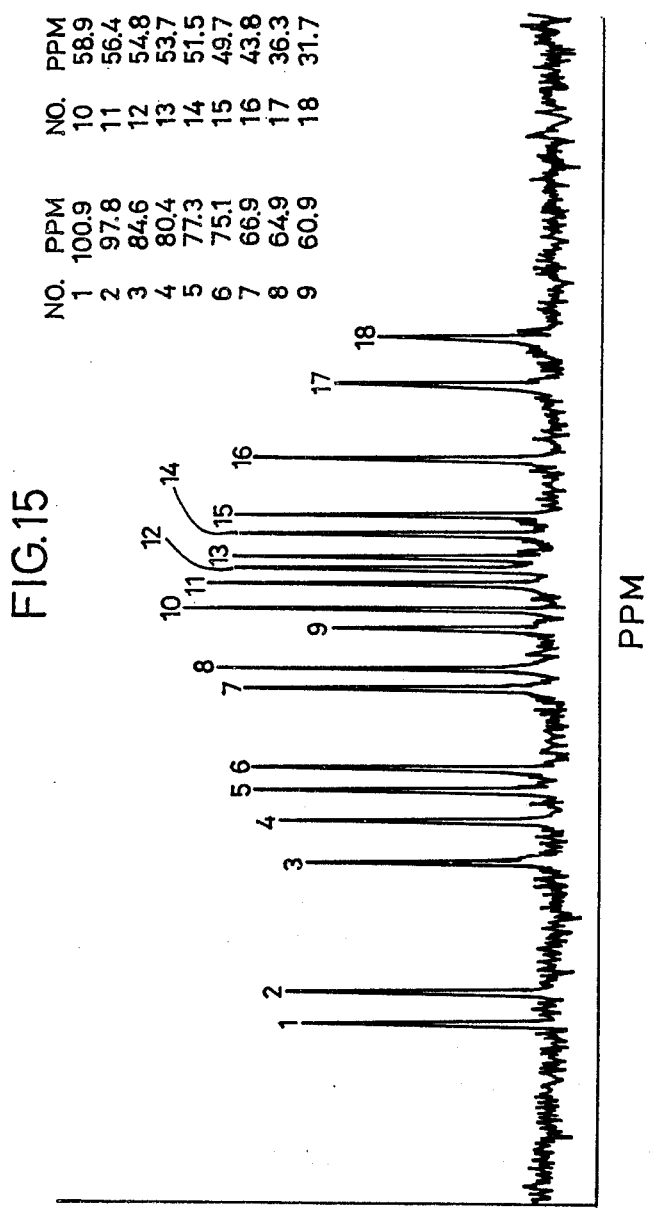

ANTIBIOTICS DESIGNATED XK-88 SERIES AND PROCESS FOR PRODUCTION THEREOF

BACKGROUND OF THE INVENTION

The present invention relatees to novel antibiotics and a process for the production thereof. More specifically the present invention relates to novel antibiotics designated, XK-88-1, XK-88-2, XK-88-3 and XK-88-5 and a process for producing such antibiotics.

Antibiotics which exhibit activity against a borad spectrum of bacteria are always in demand. To this end, a new species of microorganism has been isolated from soil located in Tajima-cho, Hofu-shi, Yamaguchi-ken, Japan. This new species, when cultured, produces a series of new antibiotics, the XK-88 series, all of which exhibit strong antibacterial activity against various Gram-positive and Gram-negative bacteria. Accordingly, the antibiotics of the invention are useful to clean and sterilize laboratory glassware ans surgical instruments, and may also be used in combination with various soaps for sanitation purposes as in cleaning and sanitizing hospital rooms and areas used for the preparation of food.

BRIEF DESCRIPTION OF THE DRAWINGS

FIG. 15 illustrates the $C^{13}$-NMR spectrum of the sulfate of XK-88-5.

SUMMARY OF THE INVENTION

Figure 1:
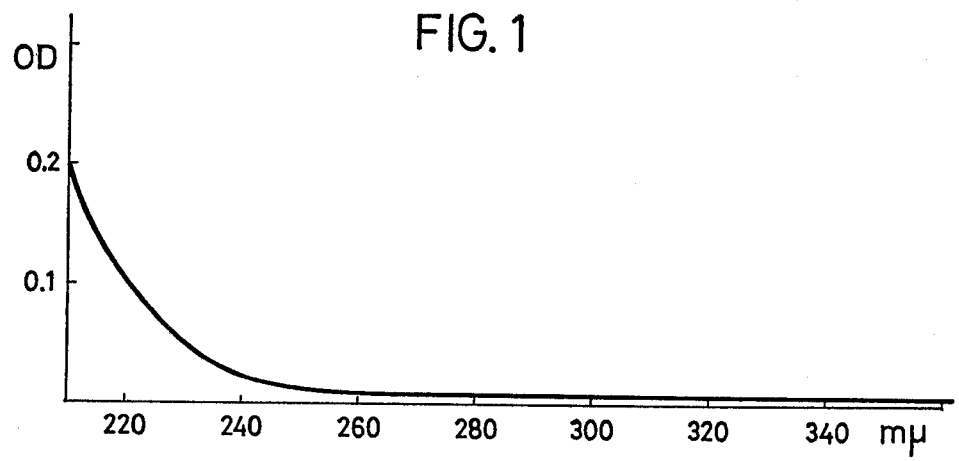
FIG. 1 illustrates the ultraviolet absorption spectrum of the sulfate of XK-88-1.

In accordance with the present invention a novel series of related antibiotics, XK-88-1, XK-88-2, XK-88-3 and XK-88-5, are produced by culturing a microorganism belonging to the genus Streptomyces, which is capable of producing the antibiotics, in a nutrient medium until substantial antibacterial activity is detected in the culture liquor. At the completion of culturing, the antibiotics are recovered respectively as active fractions by ion exchange resin treatment and further isolated as purified substances by conventional methods employed in isolation and purification.

The novel antibiotics of the present invention may be considered to have the following general formula:

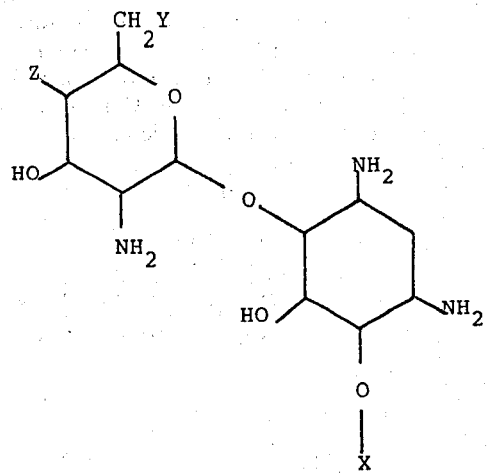

wherein X represents

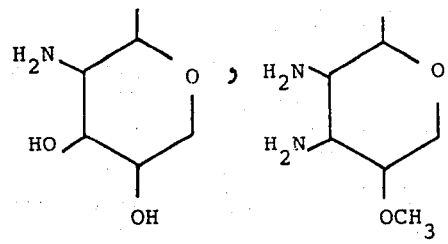

or —H; Y represents —NH$_2$ or —OH, and is —NH$_2$ when X is —H; and Z represents —H or —OH, and is —H when X is —H.

DESCRIPTION OF THE INVENTION

Antibiotics of the XK-88 series are produced by culturing a microorganism belonging to the genus Streptomyces. A particularly suitable microorganism belongs to *Streptomyces hofuensis* which is a heretofore unidentified new species. Its typical strain was originally identified as Streptomyces sp. MK-88. This strain has been deposited with the American Type Culture Collection, Rockville, Maryland, and has been accorded accession number ATCC 21970. The strain has also been deposited with the Fermentation Research Institute, Japan, and assigned the registered number FERM-P No. 2216. The MK-88 strain is characterized by the following properties:

I. Morphology:

Generally, the MK-88 strain is poor in growth. Of the eight kinds of media shown in Table 1 below, the MK-88 strain shows moderate growth only on three media, i.e. oatmeal agar, starch agar and yeast extract-malt extract agar. On the remaining media, the strain shows only slight growth. The formation of an aerial mycelium is poor and a white aerial mycelium is formed only on sucrose - nitrate agar, starch agar and yeast extract-malt extract agar. The aerial mycelium shows simple branching. A sporophore is straight or flexuous, and the top of sporophores sometimes makes a loop, but never makes spiral. Frequently, more than ten spores with a warty or spiny surface are formed at the end of the sporophore.

II. Culture Characteristics:

The degree of growth and additional characteristics observed when the MK-88 strain is cultured on various media are set forth in Table 1. The color indications are given according to the classifications in the Color Harmony Manual, 4th edition (Container Corporation of America). The characteristics are determined after culturing at 30°C. for 2 weeks.

TABLE 1

Growth on Various Media

| Medium | Growth | Substrate Mycelia | Formation of Aerial Mycelia | Aerial Mycelia | Soluble Pigments |
|---|---|---|---|---|---|
| Sucrose-Nitrate agar | Poor | Colorless to cream (1½ ca) | Poor | White (a) | None |
| Glucose-Asparagine agar | Poor | Colorless to cream (1½ ca) | | None | None |
| Nutrient agar | Poor | Colorless to yellow maple (3ng) | | None | None |
| Oatmeal agar | Moderate | Mustard gold (2 pg) to light mustard tan (2 ie) | | None | None |
| Starch agar | Moderate | Bamboo chamois (2 gc) | Poor | White (a) | None |
| Tyrosine agar | Poor | Colorless to yellow maple (3 ng) | | None | None |
| Yeast extract-malt extract agar | Moderate | Yellow maple (3 ng) | Poor | White (a) | None |
| Glycerin-Asparagine agar | Poor | Colorless to light ivory eggshell (2 ca) | | None | None |

As shown in the above Table 1, the substrate mycelia are colorless or cream-colored to brown, the aerial mycelia are white and no soluble pigments are produced on any of the media.

III. Physiological Properties:

| | |
|---|---|
| Growth temperature: | 26 to 43°C. |
| Liquefaction of gelatin: | Negative |
| Hydrolysis of starch: | Positive |
| Coagulation and peptonization of skim milk: | Negative |

Formation of melanoid pigments: No pigments are formed on tyrosine agar medium and peptone-yeast-iron agar medium.

IV. Utilization of Carbon Sources:

| Carbon Source | Utilization |
|---|---|
| D-Glucose | ++ |
| Saccharose | ++ |
| Mannitol | ++ |
| D-Xylose | ++ |
| L-Rhamnose | ++ |
| D-Arabinose | ± |
| Inositol | − |
| D-Fructose | − |

-continued

| Carbon Source | Utilization |
|---|---|
| D-Raffinose | − |

Strains of species characterized by the following properties were searched for in the The Actinomycetes, S. A. Waksman, The Williams & Wilkins Co., 1961, Vol. 2 and International Journal of Systematic Bacteriology Vol. 18 No. 2 p 69–189, Vol. 18 No. 4 p 279–392, Vol. 19 No. 4 p 391–512, Vol. 22 No. 4 p 265–394: simple branching; formation of no melanoid pigments nor soluble pigments; straight, flexuous or loopy sporophore; warty or spiny spore surface, white aerial mycelium; and colorless or yellowish brown substrate mycelium which never exhibits any other distinct color. As a result, the MK-88 strain was determined to be similar to the strains of Streptomyces craterifer and Streptomyces bluensis, particularly, the strains of the former species. However, the MK-88 strain has properties different from those of the aforementioned two species as is illustrated by the following Table 2.

Table 2

| S. craterifer | S. bluensis | MK-88 |
|---|---|---|
| The sphorophore rarely forms spiral | The sporophore rarely forms spiral | The sporophore forms no spiral under the same culture conditions as those of the two strains of S. craterifer and S. bluensis |
| Aerial mycelium is formed on oatmeal agar medium and glycerin-asparagine agar medium | Aerial mycelium is formed on oatmeal agar medium and glycerin-asparagine agar medium | No aerial mycelium is formed on oatmeal agar medium and glycerin-asparagine agar medium |
| | Aerial mycelium is sometimes colored blue on yeast extract-malt extract agar medium Inositol, fructose and raffinose are utilized | Aerial mycelium is colored white on yeast extract-malt extract agar medium Inositol, fructose and raffinose are not utilized |

On the basis of the above observations, the MK-88 strain is considered as belonging to a new species and this species is named Streptomyces hofuensis after the name of the place where the strain had been isolated.

As is the case with other strains of the Actinomycetes, the microorganism useful in carrying out the present invention can be mutated by artificial means such as ultra-violet irradiation, $Co^{60}$ irradiation, X-ray irradiation and the action of various mutation-inducing chemicals. Accordingly, any strain, even if thus mutated, is contemplated as appropriate for the present invention insofar as it has the ability to produce any one or all of the antibiotics of the XK-88 series.

Generally, conventional methods for culturing microorganisms of the Actinomycetes may be used in the process of the present invention. Various nutrient sources may be employed for a culture medium. As a carbon source, glucose, starch, mannose, sucrose, molasses, vegetable oil, etc. may be used alone or in combination. Additionally, hydrocarbons, alcohols, organic acids, etc. may be used as a carbon source depending upon the ability of utilization possessed by the microorganism. Inorganic and organic nitrogen sources such as ammonium chloride, ammonium sulfate, urea, ammonium nitrate, sodium nitrate, etc. and natural nitrogen sources such as peptone, meat extract, yeast extract, dry yeast, corn steep liquor, soybean powder, casamino acid, soluble vegetable protein, etc. may be used alone or in combination. In addition, such inorganic salts as sodium chloride, potassium chloride, calcium carbonate, phosphates, etc. may be added to the medium, if necessary. Furthermore, organic or inorganic materials capable of promoting growth of the particular microorganism and thus enhancing production of the antibiotic of the invention may be properly added to the medium.

A liquid culturing method, especially a submerged stirring culturing method, is most suitable for the process of the invention. It is desirable to carry out the culturing at a temperature of 26° to 43°C and at approximately neutral pH. Antibiotics of the XK-88 series are formed and accumulated in the culture liquor usually after 2 to 15 days of culturing. When the yield of XK-88 antibiotics in the culture liquor reaches a maximum, culturing is discontinued and the desired product is isolated and purified from the culture liquor after the microbial cells have been removed such as by filtration.

Isolation and purification of XK-88 antibiotics from the filtrate are carried out according to methods usually used for the isolation and purification of microbial metabolic products from culturre liquor.

Since members of the XK-88 series are basic and are well soluble in water, but poorly soluble in ordinary organic solvents, the desired products can be purified by methods usually used for the purification of so-called water-soluble basic antibiotics. More specifically, the members of the XK-88 series may be purified by a proper combination of adsorption and desorption from cation exchange resins and active carbon; column chromatography using cellulose; adsorption and desorption from Sephadex (trade name, produced by Pharmacia Fine Chemicals Inc., Sweden) LH-20 column; silica gel chromatography; and the like methods.

For example, the cell free culture filtrate is first adjusted to a pH of 7.5 and then subjected; to adsorption on a cation exchange resin, Amberlite (trade name, produced by Rohm & Haas Co., U.S.A.) IRC-50 ($NH_4^+$ form). After washing with water, elution is carried out with 0.5N aqueous ammonia. The active fraction is concentrated under reduced pressure. The concentrate is then adjusted to a pH of 7.5 and passed through a column packed with active carbon. The column is washed with a small amount of water and then eluted with 0.5N sulfuric acid. Colored impurities are scarcely eluted. The eluate is adjusted to a pH of 7.0 with Dowex (Trade name, produced by the Dow Chemical Co., U.S.A.) 44 ($OH^-$ form) and passed through a column of Amberlite CG-50 ($NH_4^+$ form). After washing with water, elution is carried out with 0.2N aqueous ammonia.

As a result, the XK-88-1 component is first eluted, followed by the XK-88-3 component and then the Xk-88-5 component. The XK-88-2 component may then be eluted with 0.5N aqueous ammonia.

The fraction containing XK-88-1 as the main component is concentrated. The concentrate is passed through a column of silica gel. Elution is carried out with 50% aqueous methanol. Fractions containing active substance exhibiting Rf values of 0.58 and 0.31 in silica gel thin layer chromatography using developer II [methanol and 10% aqueous ammonium acetate (1:1)] and developer M [n-butanol, ethanol, chloroform and 17% aqueous ammonia (4:5:2:5)] respectively, are combined and concentrated. The concentrate is adjusted to a pH of 7.5 and then passed through a column of Amberlite CG-50 ($NH_4^+$ form). After washing with water, elution is carried out with 0.2N aqueous ammonia. The active fractions are concentrated and the concentrate is adjusted to pH of 4.5 with sulfuric acid. Methnal is added thereto, whereby a white powder of the sulfate of XK-88-1 is obtained.

The fractions containing XK-88-3 and XK-88-5 as main components are concentrated. The concentrate is passed through a column of silica gel. Any contamination by the XK-88-1 component is first eluted out with 50% aqueous methanol. Then, the XK-88-3 component which exhibits Rf values of 0.39 and 0.27 respectively in silica gel thin layer chromatography using developer II and developer M, is eluted out with a mixture of methanol and 10% aqueous ammonium acetate (1:1). The XK-88-5 component (Rf 0.20 and Rf 0.50 in silica gel thin layer chromatography using developer II and developer M, respectively) is successively eluted out. The active fraction containing XK-88-3 as a main component and that fraction containing XK-88-5 as a main component are respectively passed through a column of Amberlite CG-50 ($NH_4^+$ form). After washing with water, elution is carried out with 0.5N aqueous ammonia. Each of the active fractions is concentrated and passed through a column of silica gel. By carrying out elution with a solvent mixture of n-butanol, ethanol, chloroform, 17% aqueous ammonia (4:5:2:5), the active fraction containing XK-88-3 as a single component and the active fraction containing XK-88-5 as a single component are obtained respectively. Each of the active fractions is concentrated and passed through a column of Amberlite CG-50 ($NH_4^+$ form). After washing with water, elution is carried out with 0.5N aqueous ammonia. Each of the active fractions is concentrated and adjusted to a pH of 4.5 with sulfuric acid. Methanol is added thereto, whereby a white powder of the sulfate of XK-88-3 and that of the sulfate of XK-88-5 are obtained respectively.

The active fraction containing XK-88-2 as a main component is concentrated. The concentrate is passed through a column of silica gel. Elution is carried out with a mixture of methanol and 10% aqueous ammonium acetate (1:1). As a result, the fraction containing XK-88-2 which exhibits Rf values of 0.45 and 0.38 in silica gel thin layer chromatography using developer II and developer M, respectively, is obtained. The active fraction is passed through a column of Amberlite CG-50 ($NH_4^+$ form). After washing with water, elution is carried out with 0.5N aqueous ammonia. The eluted active fraction is concentrated and passed through a column of silica gel. By carrying out elution with a solvent mixture of n-butanol, ethanol, chloroform and 17% aqueous ammonia (4:5:2:5), the active fraction containing XK-88-2 as a single component is obtained. The active fraction is concentrated and ajdusted to a pH of 7.5. The concentrate is then passed through a column of Amberlite CG-50 ($NH_4^+$ form). After washing with water, elution is carried out with 0.5N aqueous ammonia. The eluted active fraction is concentrated and adjusted to a pH of 4.5 with sulfuric acid. Methanol is added thereto, whereby a white powder of the sulfate of XK-88-2 is obtained.

When colored impurities are contained in an XK-88 component or in a mixture of components, decolorization may be carried out by treatment with granular active carbon, a porous resin such as Diaion HP-10 (trade name, produced by Mitsubishi Kasei Co., Ltd., Japan) and Amberlite XAD-2, and an anion exchange resin such as Dowex 1x2 (OH⁻ form), etc. More specifically, an aqueous solution of a member of the XK-88 series or a mixture thereof, which contains colored impurities, is passed through a column of Diaion HP-10. By carrying out elution with water, an aqueous solution of a member of XK-88 or a mixture thereof free of the colored impurities can be obtained.

During the above-mentioned step of purification, the behavior of the members of the XK-88 series is checked by ascending thin layer chromatography on a plate of silica gel using developers II [methanol and 10% aqueous ammonium acetate (1:1)] and M [n-butanol, ethanol, chloroform and 17% aqueous ammonia (4:5:2:5)]. Development is carried out at room temperature for 3 to 4 hours. The Rf values of XK-88-1, -2, -3 and -5 on a thin layer chromatogram are shown in Table 3, set forth hereinafter.

THE ANTIBIOTICS

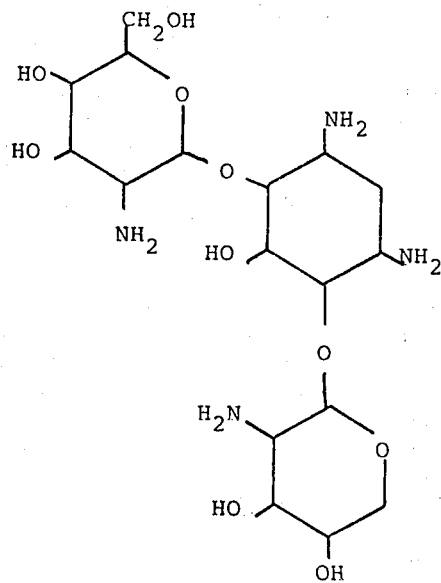

XK-88-1

The sulfate of XK-88-1 is a white crystalline powder. The melting point of the sulfate is 200°–240°C. (decomposition). The optical rotation of the sulfate is $[\alpha]_D^{28} = +77.9°$ (C = 1.08, H$_2$O). As a result of the measurement of a high resolution mass spectrum, XK-88-1 (free base) is determined to have a molecular weight of 454 and a molecular formula of $C_{17}H_{34}N_4O_{10}$. An elementary analysis of the sulfate of XK-88-1 reveals: C = 29.35%, H = 6.48%, N = 8.35% (Calculated for $C_{17}H_{34}N_4O_{10} \cdot 2H_2SO_4 \cdot 3H_2O$: C = 29.23%, H = 6.35%, N = 8.02%).

Figure 2:
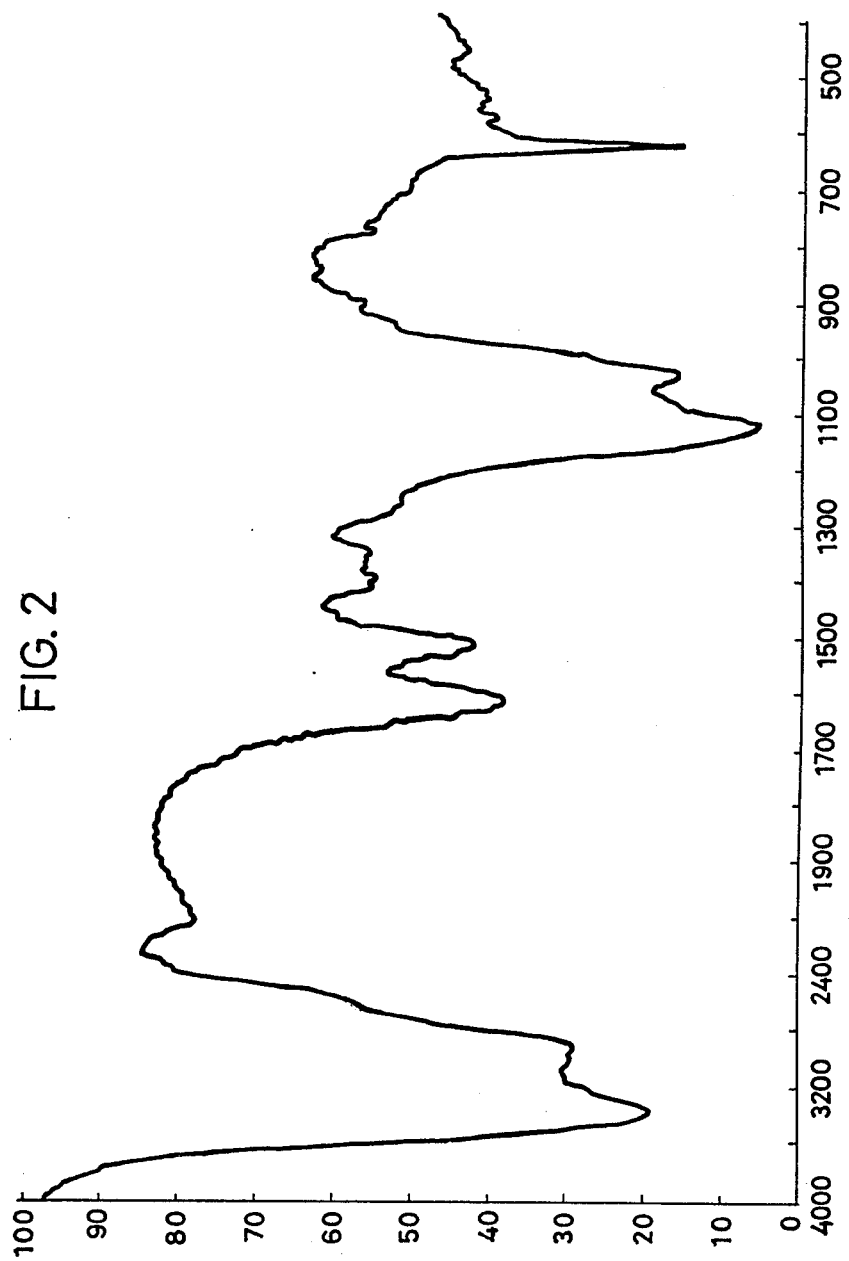
FIG. 2 illustrates the infrared absorption spectrum of the sulfate of XK-88-1.

The ultraviolet absorption spectrum of an aqueous solution of the sulfate of XK-88-1 (FIG. 1) reveals no characteristic absorption maximum between 220–360 m$\mu$ but only shows a terminal absorption. The infrared absorption spectrum of the same (as KBr tablet) is illustrated in FIG. 2. As is apparent from the figure, XK-88-1, shows peaks at the following wavelengths expressed in reciprocal centimeters (cm⁻¹):

3355, 2900, 2000, 1610, 1505, 1120, 1025, 615

Figure 9:
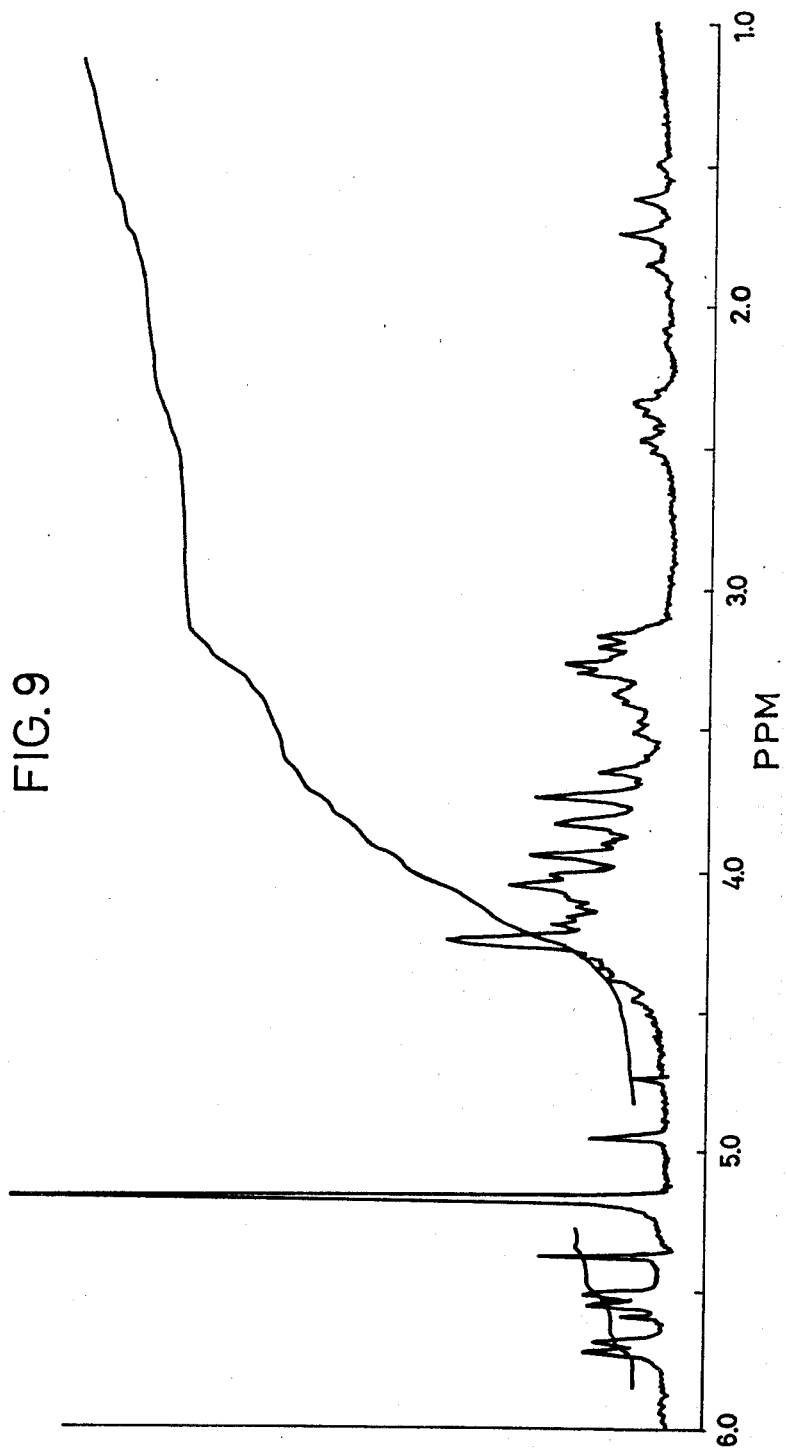
FIG. 9 illustrates the NMR spectrum of the free base of XK-88-1.
Figure 13:
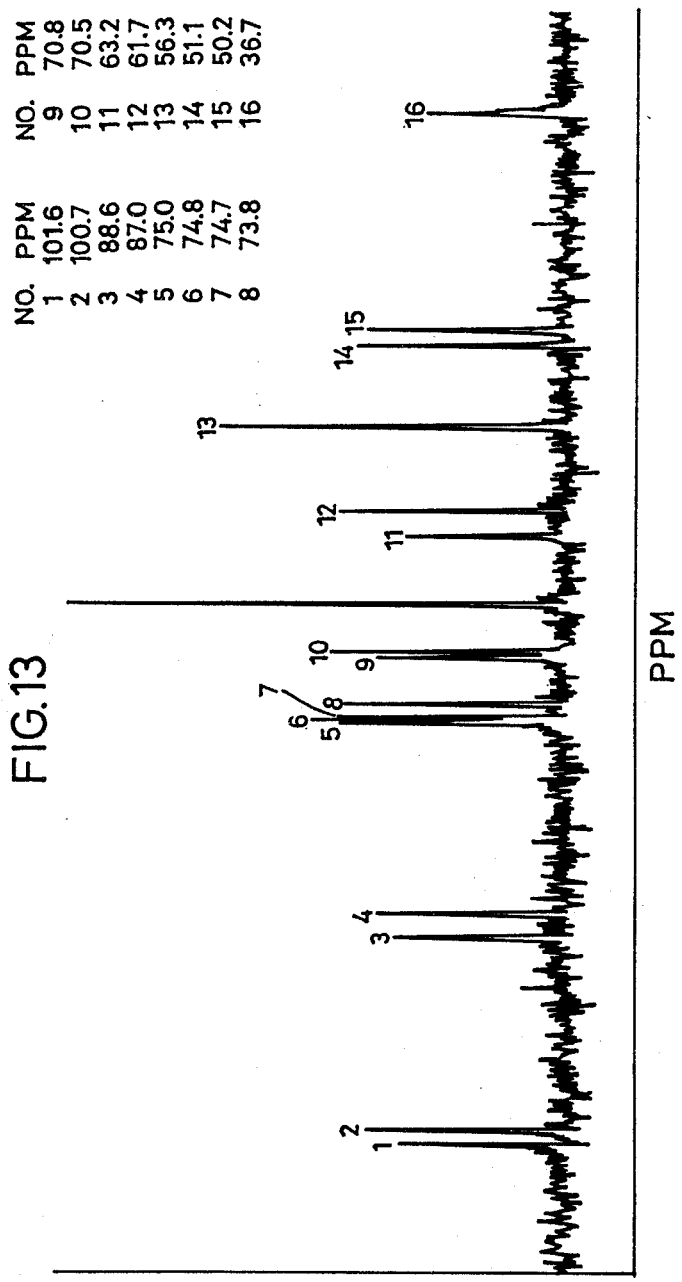
FIG. 13 illustrates the $C^{13}$-NMR spectrum of the sulfate of XK-88-1.

FIG. 9 illustrates the characteristic NMR (proton) spectrum of the free base of XK-88-1. FIG. 13, on the other hand, illustrates the C¹³ - NMR spectrum of the free base of XK-88-1.

With regard to color tests, the sulfate of XK-88-1 gives positive reactions in the ninhydrin test and Rydon-smith test (H. N. Rydon et al, Nature 169 922, 1952), and gives negative reactions in the Sakaguchi test, maltol test, ferric chloride test, Fehling test and biuret test.

The sulfate of XK-88-1 is very soluble in water, poorly soluble in methanol and ethanol, and insoluble in such organic solvents as acetone, ethyl acetate, ethyl ether, chloroform, etc.

Based upon the foregoing, XK-88-1 is believed to have the following chemical structure:

XK-88-2

The sulfate of XK-88-2 is a white powder. The melting point of the sulfate is 225°–250°C (decomposition). The optical rotation of the sulfate is $[\alpha]_D^{28} = +74.7°$ (C = 0.56, H$_2$O). As a result of the measurement of a high resolution mass spectrum, XK-88-2 (free base) is determined to have a molecular weight of 306 and a molecular formula of $C_{12}H_{26}N_4O_5$. An elementary analysis of the sulfate of XK-88-2 reveals: C = 25.47%, H = 6.76%, N = 9.68% (Calculated for $C_{12}H_{26}N_4O_5 \cdot 2H_2SO_4 \cdot 3H_2O$: C = 25.90%, H = 6.52%, N = 10.07%).

Figure 3:
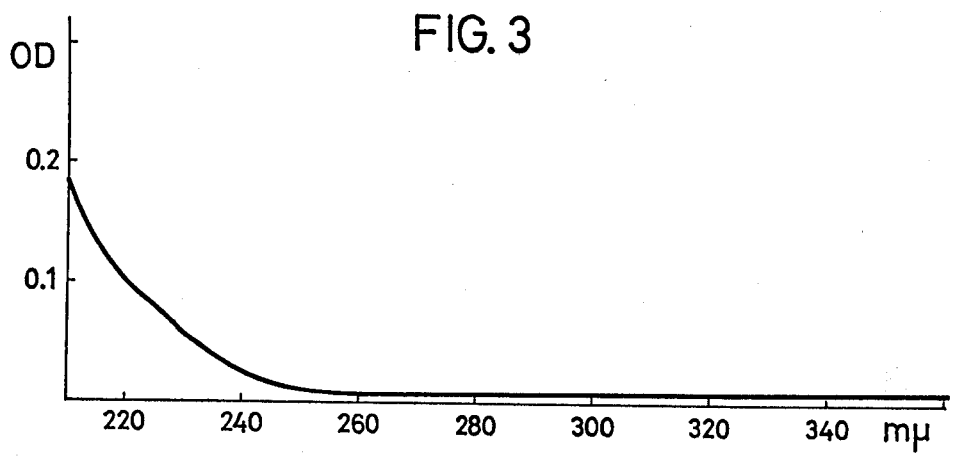
FIG. 3 illustrateds the ultraviolet absorption spectrum of the sulfate of XK-88-2.
Figure 4:
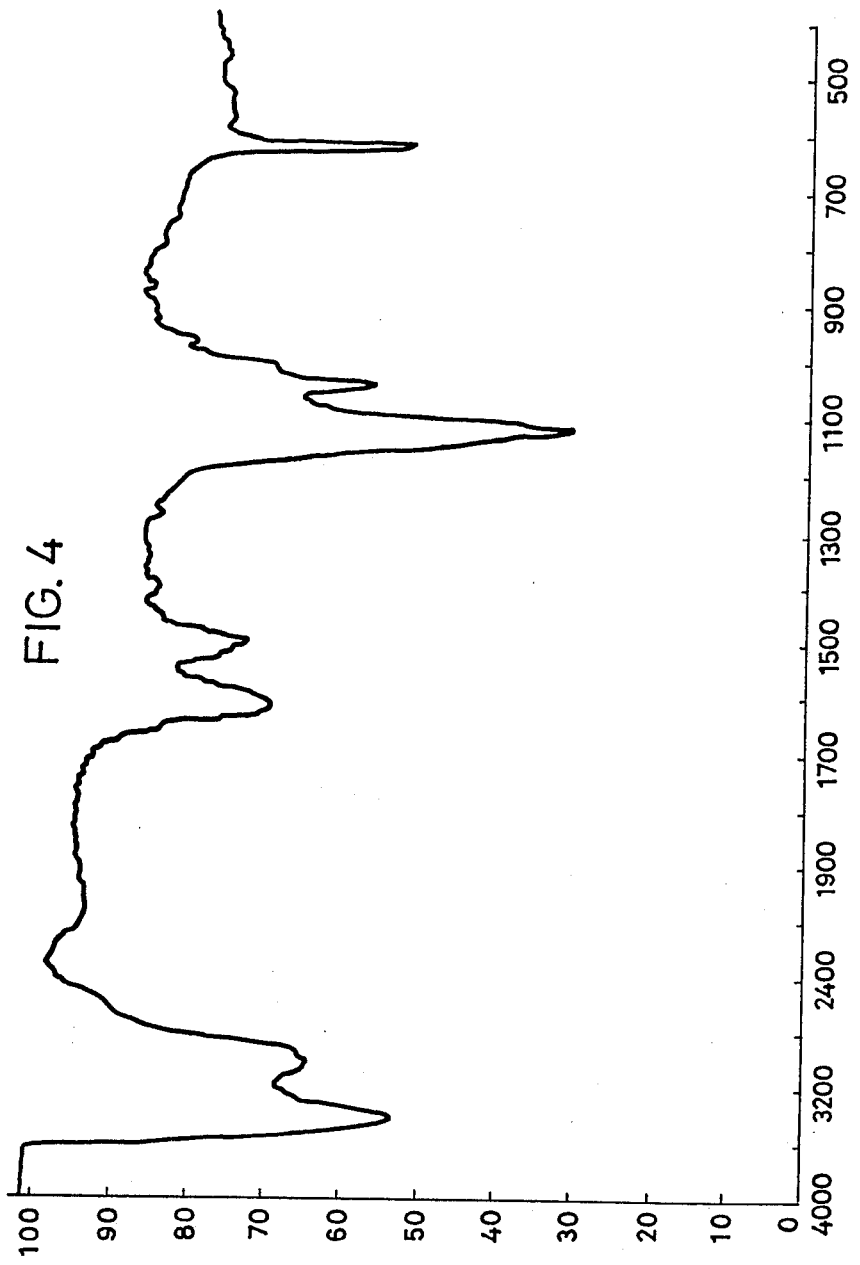
FIG. 4 illustrates the infrared absorption spectrum of the sulfate of XK-88-2.

The ultraviolet absorption spectrum of an aqueous solution of the sulfate of XK-88-2 (FIG. 3) reveals no characteristic absorption maximum between 220–360 m$\mu$, but only shows a terminal absorption. The infrared absorption spectrum of the sulfate of XK-88-2 (as KBr tablet) is illustrated in FIG. 4. As is apparent from the figure, XK-88-2 shows peaks at the following wavelengths expressed in reciprocal centimeters (cm⁻¹):

3400, 3000, 1605, 1490, 1115, 1035, 605

Figure 10:
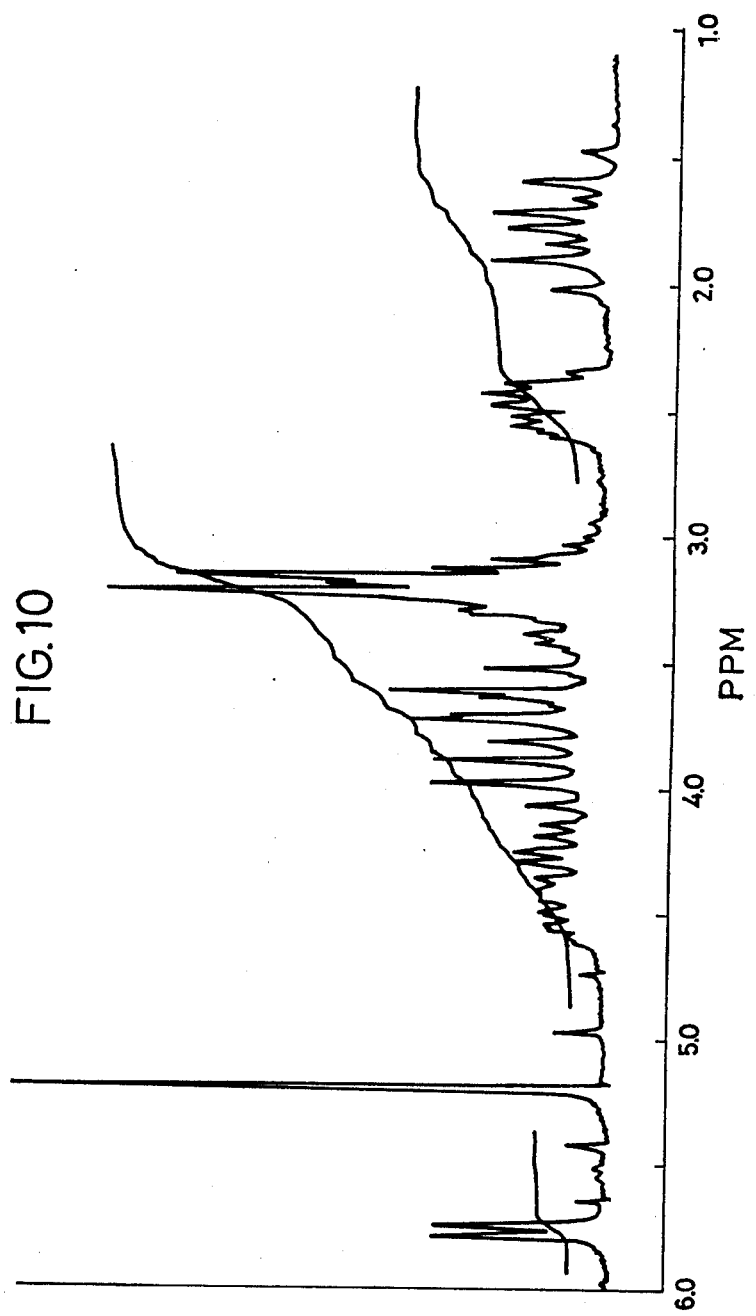
FIG. 10 illustrates the NMR spectrum of the free base of XK-88-2.
Figure 14:
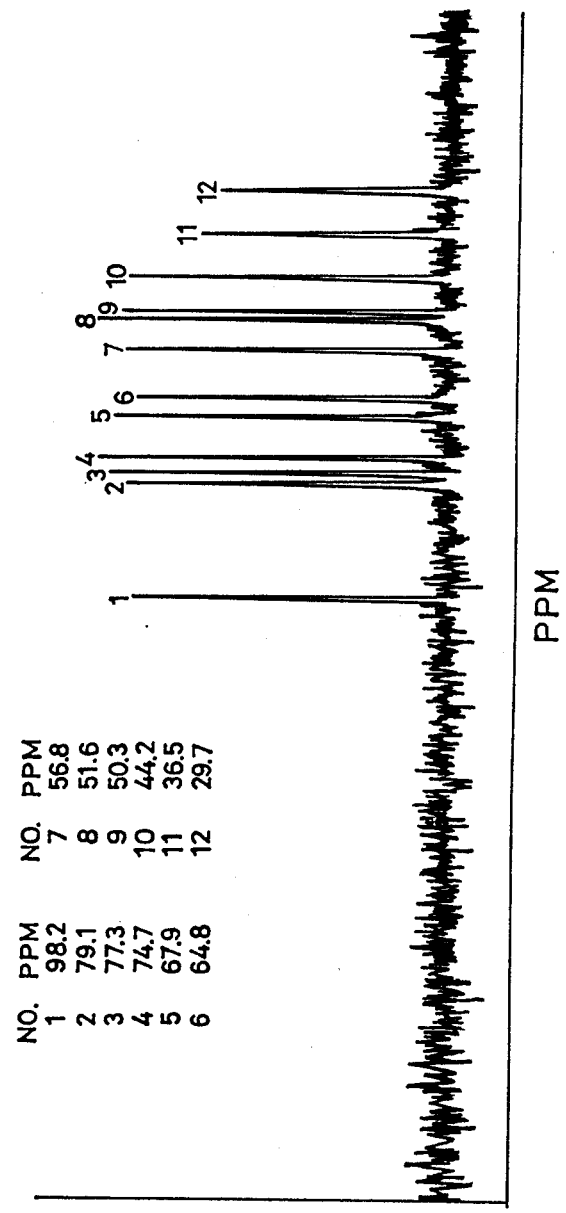
FIG. 14 illustrates the $C^{13}$-NMR spectrum of the free base of XK-88-2.

The characteristics of XK-88-2 is further confirmed by the C¹³ - NMR spectrum of the sulfate and the NMR spectrum of the free base as illustrated in FIGS. 14 and 10 respectively.

With regard to color tests, the sulfate of XK-88-2 gives positive reactions in the ninhydrin test and Rydon-Smith test, and gives negative reactions in the Sakaguchi test, maltol test, ferric chloride test, Fehling test and biuret test.

The sulfate of XK-88-2 is very soluble in water, poorly soluble in methanol and ethanol, and insoluble in such organic solvents as acetone, ethyl acetate, ethyl ether, chloroform, etc.

Based upon the foregoing, XK-88-2 is believed to have the following chemical structure:

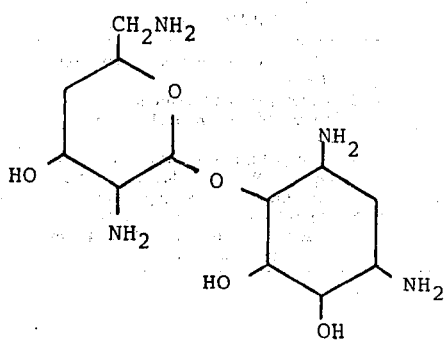

XK-88-3

The sulfate of XK-88-3 is a white powder. The melting point of the sulfate is 215°–240°C (decomposition). The optical rotation of the sulfate is $[\alpha]_D^{28} = +87.3°$ (C = 0.53, H$_2$O). As a result of the measurement of a high resolution mass spectrum, XK-88-3 (free base) is determined to have a molecular weight 453 and a molecular formula of $C_{17}H_{35}N_5O_9$. An elementary analysis of the sulfate of XK-88-3 reveals: C = 26.02%, H = 6.72%, N = 8.61% (Calculated for $C_{17}H_{35}N_5O_9 \cdot 5/2H_2SO_4 \cdot 5H_2O$: C=25.89%, H=6.39%, N=8.88%).

Figure 5:
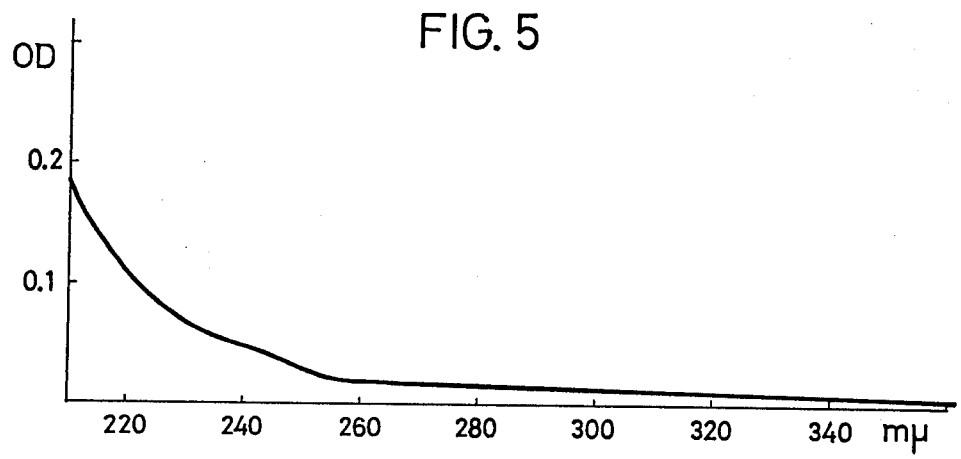
FIG. 5 illustrates the ultraviolet absorption spectrum of the sulfate of XK-88-3.
Figure 6:
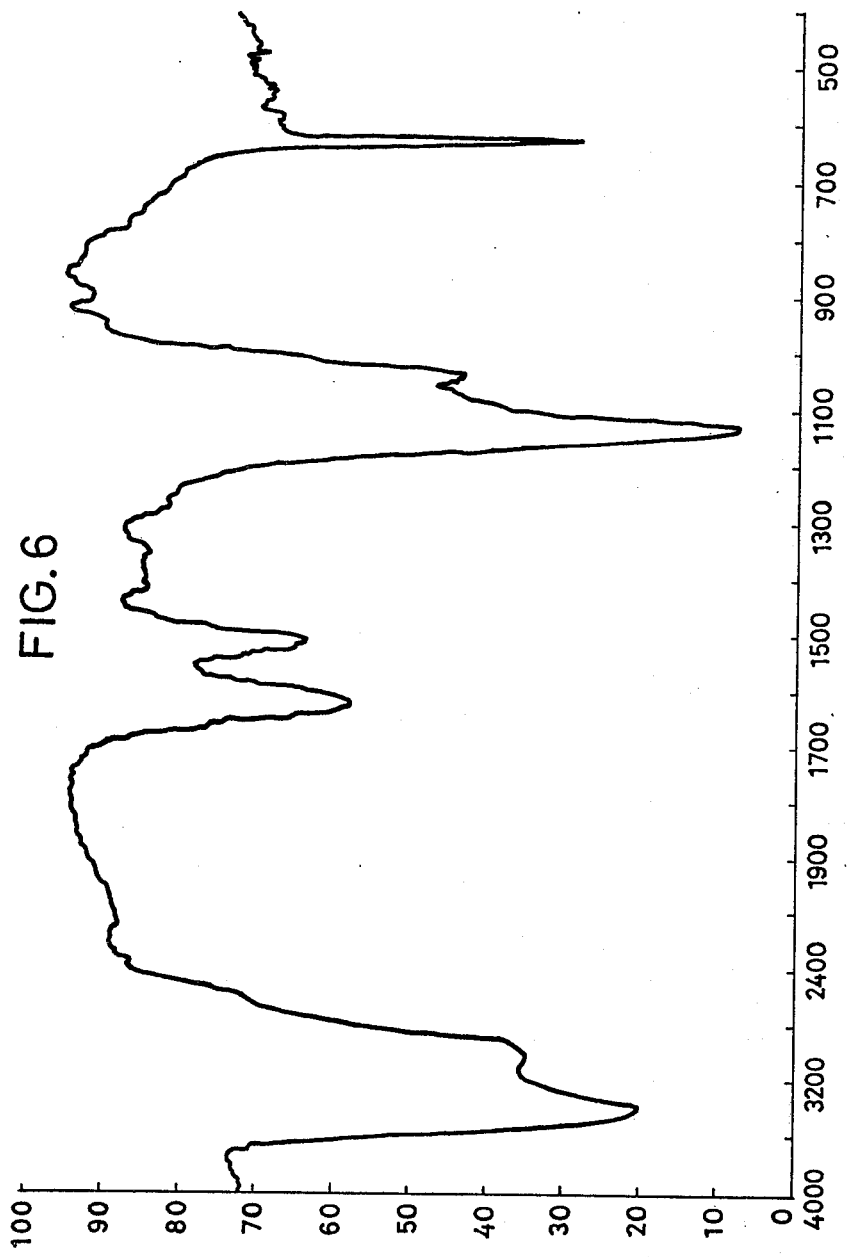
FIG. 6 illustrates the infrared absorption spectrum of the sulfate of XK-88-3.

The ultraviolet absorption spectrum of an aqueous solution of the sulfate of XK-88-3 (FIG. 5) reveals no characteristic absorption maximum between 220–360 mµ, but only shows a terminal absorption. The infrared absorption spectrum of the sulfate of XK-88-3 (as KBr tablet) is illustrated in FIG. 6. As is apparent from the figure, XK-88-3 shows peaks at the following wavelengths exprssed in reciprocal centimeters (cm$^{-1}$):

3400, 3000, 1615, 1505, 1125, 1030, 620

Figure 11:
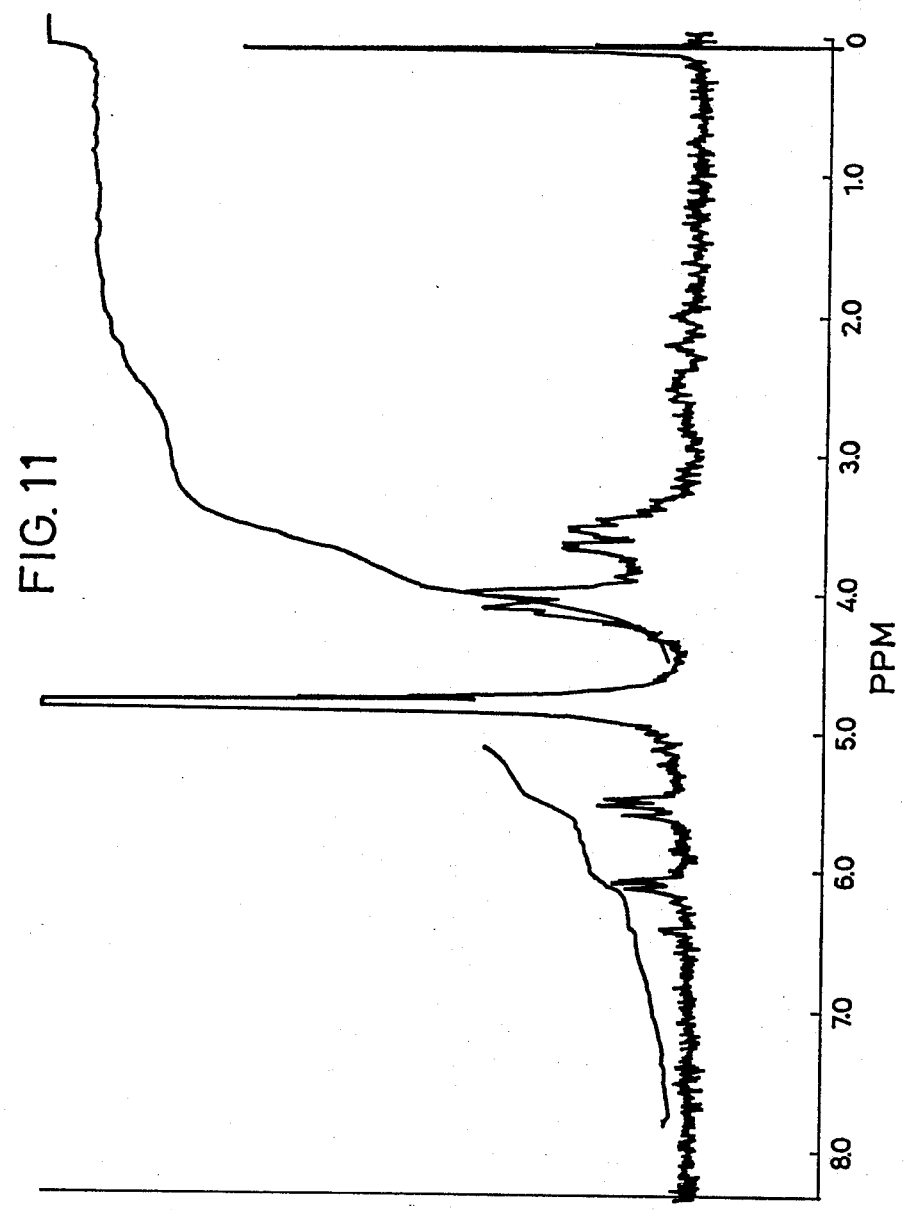
FIG. 11 illustrates the NMR spectrum of the free base of XK-88-3.

Further confirmation of the characteristics of XK-88-3 is derived from FIG. 11 which illustrates the NMR (proton) spectrum of the free base of XK-88-3.

With regard to color tests, the sulfate of XK-88-3 gives positive reactions in the ninhydrin test and Rydon-Smith test, and gives negative reactions in the Sakaguchi test, maltol test, ferric chloride test, Fehling test and biuret test.

The sulfate of XK-88-3 is very soluble in water, poorly soluble in methanol and ethanol, and insoluble in such organic solvents as acetone, ethyl acetate, ethyl ether, chloroform, etc.

Based upon the foregoing, XK-88-3 is believed to have the following chemical structure:

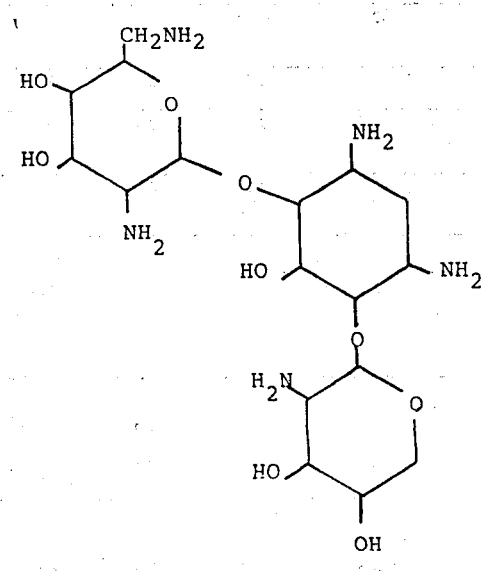

XK-88-5

The sulfate of XK-88-5 is a white powder. The melting point of the sulfate is 215°–240°C (decomposition). The optical rotation of the sulfate is $[\alpha]_D^{28} = +93.9°$ (C = 0.54, H$_2$O). As a result of the measurement of a high resolution mass spectrum, XK-88-5 (free base) is determined to have a molecular weight of 450 and a molecular formula of $C_{18}H_{38}N_6O_7$. The elementary analysis of the sulfate of XK-88-5 reveals: C = 25.89%, H = 6.50%, N = 9.74% (Calculated for $C_{18}H_{38}N_6O_7 \cdot 3H_2SO_4 \cdot 6H_2O$: C=25.35%, H=6.62%, N=9.85%).

Figure 7:
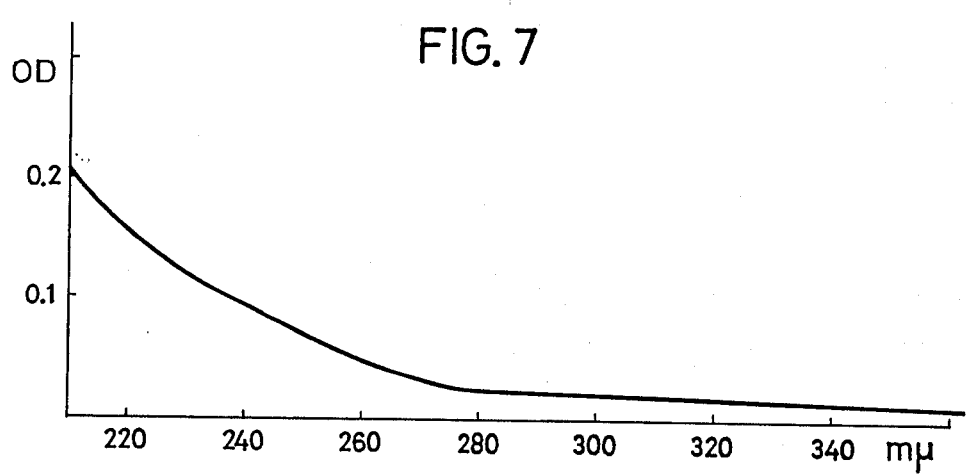
FIG. 7 illustrates the ultraviolet absorption spectrum of the sulfate of XK-88-5.
Figure 8:
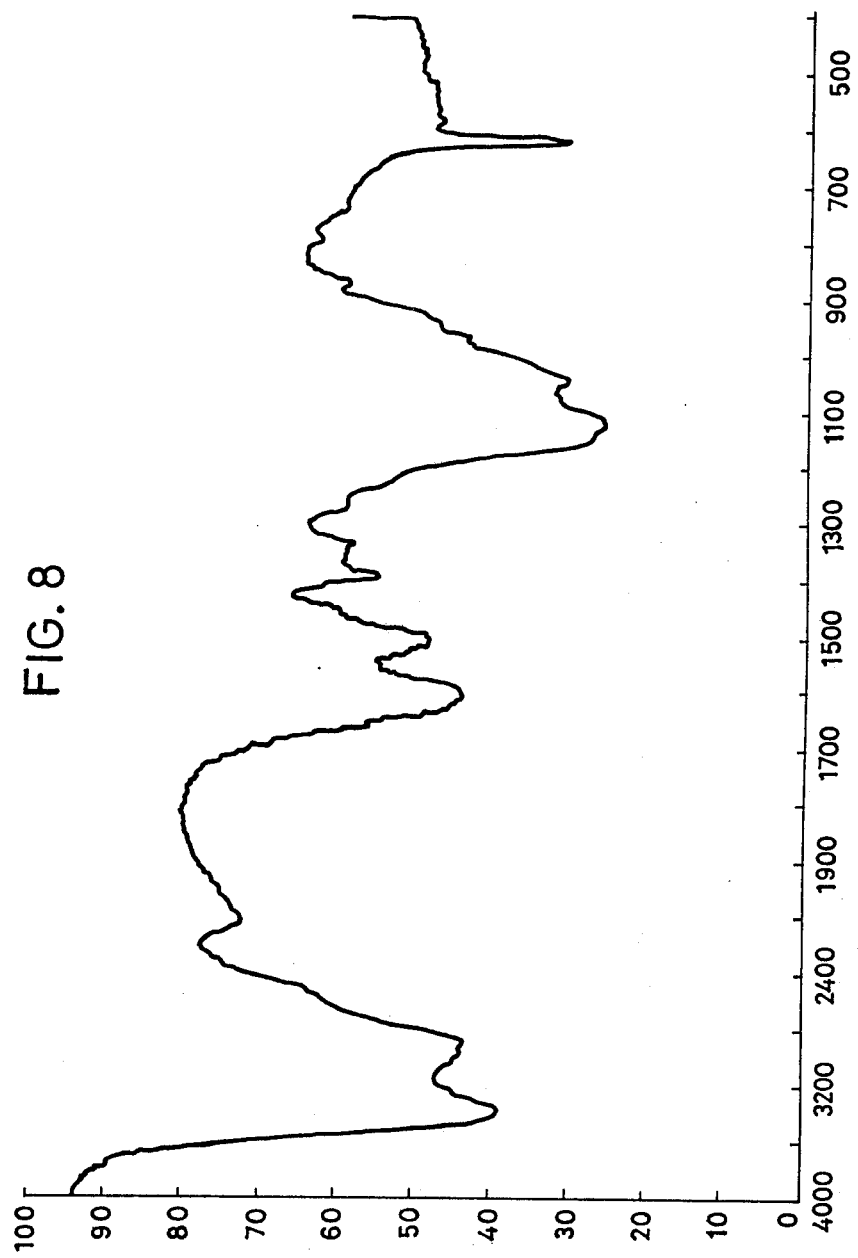
FIG. 8 illustrates the infrared absorption spectrum of the sulfate of XK-88-5.

The ultraviolet absorption spectrum of an aqueous solution of the sulfate of XK-88-5 (FIG. 7) reveals no characteristic absorption maximum between 220–360 mµ, but only shows a terminal absorption. The infrared absorption spectrum of the sulfate of XK-88-5 (as KBr tablet) is illustrated in FIG. 8. As is apparent from the figure, XK-88-5 shows peaks at the following wavelengths expressed in reciprocal centimeters (cm$^{-1}$):

3400, 2900, 1600, 1500, 1390, 1110, 1040, 610

Figure 12:
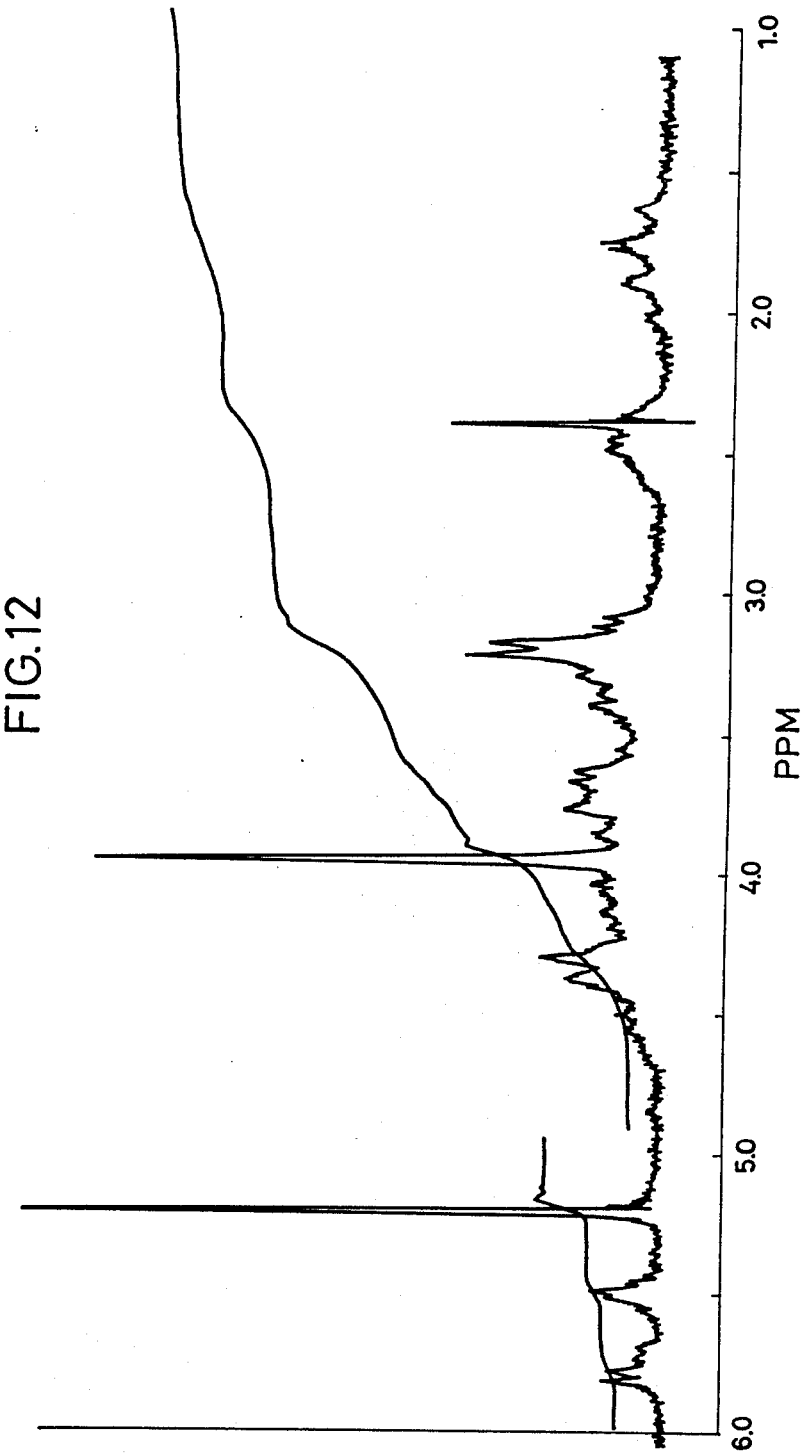
FIG. 12 illustrates the NMR spectrum of the free base of XK-88-5.

Further confirmation of the characteristics of XK-88-5 is derived from FIGS. 12 and 15 which illustrate the NMR (proton) spectrum of the free base and the $C^{13}$-NMR spectrum of the sulfate respectively.

With regard to color tests, the sulfate of XK-88-5 gives positive reactions in the ninhydrin test and Rydon-Smith test, and gives negative reactions in the Sakaguchi test, maltol test, ferric chloride test, Fehling test and biuret test.

The sulfate of XK-88-5 is very soluble in water, poorly soluble in methanol and ethanol, and insoluble in such organic solvents as acetone, ethyl acetate, ethyl ether, chloroform, etc.

Based upon the foregoing, XK-88-5 is believed to have the following chemical structure:

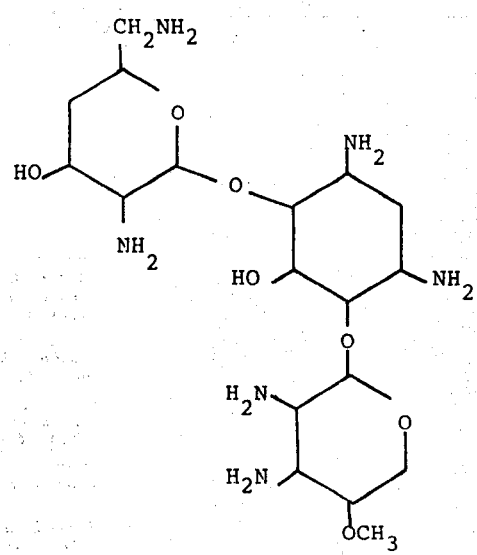

Included in the composition of matter aspect of the present invention are the pharmaceutically acceptable acid addition salts of the components of the XK-88 series which can be made, according to known procedures, by neutralizing the free base with the appropriate acid to below a pH of 7.0 and preferably to a pH of about 2 to 6. Suitable acids for this purpose are such as hydrochloric, sulfuric, phosphoric, thiocyanic, fluorosilic, hexafluoroarsenic, hexafluorophosphoric, acetic, succinic, citric, camphoric, glutaric, glycolic, phthalic, tartaric, lauric, stearic, salicylic, etc.

The physical embodiments of the acid solution salts are characterized by being white powders which are soluble in water, poorly soluble or insoluble in most organic solvents.

The Rf values of the antibiotics of the XK-88 series obtained as a result of paper chromatography and thin layer chromatography using various developers are shown in the following Table 3. These values are compared with the Rf values of various similar antibiotics developed in the same manner.

Developer
- I: chloroform : methanol : 17% aqueous ammonia (2:1:1 the upper layer of the mixture)
- II: methanol : 10% ammonium acetate (1:1)
- M: n-butanol : ethanol : chloroform : 17% aqueous ammonia (4:5:2:5)

-continued

1: 20% aqueous solution of ammonium chloride
2: Water-saturated n-butanol
3: n-butanol : acetic acid : water (3:1:1)
4: water-saturated n-butanol containing 2% (W/V) p-toluene sulfonic acid and 2% (V/V) piperidine
5: chloroform : methanol : 17% aqueous ammonia (2:1:1 the lower layer of the mixture)

Table 3

|  | Rf value | | | | | | | |
|---|---|---|---|---|---|---|---|---|
|  | Silica gel thin layer chromatography | | | Paper chromatography (ascending method) | | | | |
|  | | | | Developer | | | | |
|  | I | II | M | 1 | 2 | 3 | 4 | 5 |
| XK-88-1 | 0.80 | 0.58 | 0.31 | 0.97 | 0.00 | 0.10 | 0.00 | 0.00 |
| XK-88-2 | 0.73 | 0.45 | 0.38 | 0.98 | 0.00 | 0.08 | 0.00 | 0.00 |
| XK-88-3 | 0.75 | 0.39 | 0.27 | 0.97 | 0.00 | 0.00 | 0.00 | 0.00 |
| XK-88-5 | 0.81 | 0.20 | 0.50 | 0.75 | 0.00 | 0.05 | 0.00 | 0.01 |
| Gentamicin A | 0.66 | 0.39 | 0.38 | 0.98 | 0.00 | 0.05 | 0.00 | 0.00 |
| Gentamicin B | 0.75 | 0.38 | 0.28 | 0.98 | 0.00 | 0.08 | 0.00 | 0.00 |
| Gentamicin $C_{1a}$ | 0.86 | 0.18 | 0.52 | 0.98 | 0.02 | 0.08 | 0.05 | 0.18 |
| Gentamicin $C_1$ | 0.87 | 0.17 | 0.59 | 0.98 | 0.03 | 0.08 | 0.08 | 0.59 |
| Gentamicin $C_2$ | 0.86 | 0.18 | 0.61 | 0.98 | 0.02 | 0.03 | 0.09 | 0.38 |
| Sisomicin | 0.89 | 0.66 | — | 0.98 | 0.00 | 0.06 | 0.10 | 0.18 |
| Kanamycin A | 0.77 | 0.76 | 0.15 | 0.92 | 0.00 | 0.00 | 0.00 | 0.02 |
| Kanamycin B | 0.80 | 0.80 | 0.16 | 0.98 | 0.00 | 0.00 | 0.00 | 0.01 |
| Kanamycin C | 0.84 | 0.84 | 0.17 | 0.96 | 0.00 | 0.00 | 0.00 | 0.02 |
| Ribostamycin | 0.75 | 0.72 | 0.12 | 0.98 | 0.01 | 0.03 | 0.01 | 0.00 |
| Apramycin | 0.80 | 0.35 | 0.15 | 0.95 | 0.00 | 0.00 | 0.00 | 0.02 |
| Nebramycin factor 4 | 0.78 | 0.45 | 0.16 | 0.95 | 0.00 | 0.05 | 0.00 | 0.01 |
| Nebramycin factor 5 | 0.79 | 0.45 | 0.14 | 0.95 | 0.00 | 0.05 | 0.00 | 0.00 |
| Tobramycin | 0.80 | 0.54 | 0.25 | 0.97 | 0.00 | 0.02 | 0.02 | 0.02 |
| Neomycin A | 0.40 | 0.71 | — | 0.97 | 0.00 | 0.02 | 0.02 | 0.00 |
| NK-1003 | 0.66 | 0.91 | — | 0.93 | 0.00 | 0.05 | 0.00 | — |

The in vitro antibacterial spectra of the XK-88 antibiotics by agar dilution method (pH 8.0) is illustrated in the following Table 4:

Table 4

(Minimum Inhibitory Concentration ($\mu$g/ml) by agar dilution method (pH 8.0)

| Microorganism tested | M.I.C. ($\mu$g/ml) | | | |
|---|---|---|---|---|
|  | XK-88-1 | XK-88-2 | XK-88-3 | XK-88-5 |
| *Streptococcus faecalis* ATCC 10541 | >416.5 | >83.3 | >83.3 | 10.5 |
| *Bacillus subtilis* No. 10703 | 52.1 | 0.35 | 2.7 | 0.04 |
| *Bacillus cereus* ATCC 9634 | 6.6 | 2.7 | 2.7 | 1.31 |
| *Bacillus cereus var. mycoides* ATCC 9463 | 3.3 | 0.7 | 2.7 | 0.66 |
| *Staphylococcus aureus* ATCC 6538P | 6.6 | 0.18 | 0.18 | 0.07 |
| *Staphylococcus aureus* KY 8942 (resistant to Kanamycin, Paromomycin, Streptomycin, Gentamicin and Nebramycin) | 52.1 | 1.4 | 1.4 | 0.66 |
| *Staphylococcus aureus* KY 8950 (resistant to Streptomycin, Tetracyline, Penicillin and sulfonamide | 13.1 | 0.35 | 0.35 | 0.17 |
| *Staphylococcus aureus* KY 8956 (resistant to Streptomycin, Paromomycin, Tetracycline, Kanamycin, Nebramycin, Tobramycin and | 208.5 | 0.09 | 5.3 | <0.02 |

Table 4-continued (Minimum Inhibitory Concentration (μg/ml) by agar dilution method (pH 8.0)

M.I.C. (μg/ml)

| | | | | |
|---|---|---|---|---|
| Erythromycin) | | | | |
| Staphylococcus aureus KY 8957 (resistant to Chloramphenicol, Streptomycin, Kanamycin Paromomycin, Nebramycin, Tobramycin and Tetracycline) | 104.2 | 0.09 | 5.3 | 0.04 |
| Staphylococcus aureus KY 8953 (resistant to Streptomycin, Kanamycin Paromycin, Neomycin Tetracycline, Erythromycin) | >416.5 | 0.35 | >83.3 | 0.17 |
| Klebsiella pneumoniae ATCC 10031 | 13.1 | 0.18 | 0.05 | <0.05 |
| Escherichia coli ATCC 26 | 26.1 | 0.35 | 0.18 | 0.08 |
| Escherichia coli KY 8310 (resistant to Chloramphenicol, Streptomycin, Kanamycin, Gentamicin, Paromomycin, Nebramycin, Tobramycin, Spectinomycin and Tetracycline) | >416.5 | >83.3 | 83.3 | >41.6 |
| Escherichia coli KY 8314 (resistant to Streptomycin) | 52.1 | 1.4 | 0.35 | 0.33 |
| Escherichia coli KY 8327 (resistant to Kanamycin, Gentamicin, Nebramycin and Tobramycin) | 13.1 | 0.18 | 0.05 | 0.04 |
| Escherichia coli KY 8331 (resistant to Kanamycin, Ribostamycin, Neomycin Paromomycin, Lividomycin and Nebramycin) | >416.5 | 41.7 | 41.7 | 20.8 |
| Escherichia coli KY 8334 (resistant to Kanamycin and Tobramycin) | 1.65 | 5.3 | 5.3 | 0.66 |
| Escherichia coli KY 8348 (resistant to Streptomycin and Gentamicin) | 13.5 | 0.18 | 0.09 | 2.7 |
| Proteus vulgaris ATCC 6897 | 416.5 | 1.4 | 1.4 | 0.53 |
| Pseudomonas aeruginosa BMH No. 1 | >416.5 | 10.5 | >416.5 | 8.3 |
| Shigella sonnei ATCC 9290 | 52.1 | 1.4 | 0.35 | 0.14 |
| Salmonella typhosa ATCC 9992 | 26.1 | 0.7 | 0.18 | 0.09 |

As is apparent from the above Table 4, all of the XK-88 series of antibiotics exhibit a very strong antibacterial activity against a broad range of Gram-positive and Gram-negative bacteria. Particularly, XK-88-1, XK-88-2, XK-88-3 and XK-88-5 exhibit a strong antibacterial activity against Staphylococcus aureus and Escherichia coli which are normally resistant to various known antibiotics.

A comparison of the antibiotics of the invention with various other antibiotics further illustrates their novelty. The XK-88 series of antibiotics are all water-soluble, basic antibiotics and are dextrorotatory compounds. The ultraviolet absorption spectra only show terminal absorption and reveal no characteristic absorption maximum. The molecular weight of XK-88-1, XK-88-2, XK-88-3, and XK-88-5 (free base) is 454, 306, 453 and 450, respectively. From the foregoing, Gentamicin A, Gentamicin B, Gentamicin $C_{1a}$, Gentamicin $C_1$, Gentamicin $C_2$, Kanamycin A, Kanamycin B, Kanamycin C, Ribostamycin, Tobramycin, Apramycin, Nebramycin factor 4, Nebramycin factor 5 and Sisomycin are considered as antibiotics comparatively similar to XK-88-1, XK-88-3 and XK-88-5. Neomycin A and NK-1003 appear to be comparatively similar to XK-88-2. The Rf values of XK-88-3 in silica gel thin layer chromatography and paper chromatography (Table 3)

are very close to those of Gentamicin B but the Rf values of other members of the XK-88 series are completely different from those of the known antibiotics. The molecular weight of the free base of XK-88-3 (453) is completely different from that of the free base of Gentamicin B (486). It is also apparent from Table 4 that complete cross resistance does not always occur between XK-88-1, XK-88-2, XK-88-3, XK-88-5 and the said known antibiotics. From the foregoing, XK-88-1, XK-88-2, XK-88-3 and XK-88-5 are all considered to be novel antibiotics.

Practice of certain specific embodiments of the invention is illustrated by the following representative examples.

EXAMPLE 1

In this example, *Streptomyces hofuensis* MK-88 (FERM-P No. 2216) (ATCC 21970) is used as the seed strain. One loopful of the seed strain is inoculated in 30 ml of a first seed medium having the following composition in a 250 ml-Erlenmeyer flask and cultured at 30°C for 3 days with shaking.

| | |
|---|---|
| Soluble starch | 20 g/l |
| Polypeptone | 5 g/l |
| Yeast extract | 1 g/l |
| Calcium carbonate | 1 g/l |
| (pH: 7.0 before sterilization) | |

Then 30 ml of the first seed culture is inoculated in 300 ml of a second seed medium in a 2 l-Erlenmeyer flask provided with baffles. The composition of the second seed medium is the same as that of the first seed medium. The second seed culturing is carried out at 30°C for 2 days with shaking. Thereafter, 1.5 l of the second seed culture (corresponding to the content of 5 flasks) is inoculated in 15 l of a third seed medium in a 30 l-stainless steel jar fermenter. Again, the composition of the third seed medium is the same as that of the first seed medium.

Culturing in the jar fermenter is carried out at 30°C for 2 days with aeration (15 l/min and agitation (350 r.p.m.). Then 15 l of the third seed culture is inoculated in 100 l of a fourth seed medium in a 300 fermenter. The composition of the fourth seed medium is the same as that of the first seed medium. Culturing in the fermenter is carried out at 30°C for 2 days with aeration (100 l/min and agitation (150 r.p.m.). Finally, 100 l of the fourth seed culture is inoculated in 1,000 l of a fermentation medium in a 2,000 l-fermenter. The composition of the fermentation medium is as follows:

| | |
|---|---|
| Soluble starch | 40 g/l |
| Soybean meal | 20 g/l |
| Meat extract | 5 g/l |
| $K_2HPO_4$ | 0.5 g/l |
| $MgSO_4 \cdot 7H_2O$ | 0.5 g/l |
| KCl | 0.3 g/l |
| $CaCO_3$ | 3 g/l |
| (pH: 7.0 before sterilization) | |

Culturing is carried out at 30°C for 4 days with aeration (400 l/min.) and agitation (150 r.p.m.).

After the completion of culturing a mixture of XK-88-1, XK-88-2, XK-88-3 and XK-88-5 is accumulated in the culture liquor. The total yield calculated as antibacterial activity is 3.5 mg/l based upon the sulfate of XK-88-5.

EXAMPLE 2

In this example, 1,000 l of the culture liquor obtained in Example 1 is adjusted to a pH of 7.5 with concentrated sulfuric acid.

About 10 kg of a filter aid, Radiolite No. 600 (trade name, produced by Showa Kagaku Kogyo Co., Ltd., Japan) is added thereto and the microbial cells and insoluble matters are removed by filtration. The filtrate is passed through a column packed with about 100 l of a cation exchange resin, Amberlite IRC-50 ($NH_4^+$ form). Active substances are adsorbed on the resin. After washing with about 300 l of water, elution is carried out with 0.5N aqueous ammonia. The activity of the eluate is determined by a paper disk method on an agar plate using *Bacillus subtilis* No. 10707. The active fractions are combined and concentrated to 6 l under reduced pressure. The concentrate is adjusted to a pH of 7.5 with concentrated sulfuric acid and the precipitate is removed by filtration. The filtrate is passed through a column packed with 2 l of Amberlite IRC-50 ($NH_4^+$ form). After washing with 10 l of water, elution is carried out with 0.5N aqueous ammonia and the active fractions are combined and concentrated to about 300 ml under reduced pressure. Since the concentrate contains brown-colored impurities, it is adjusted to a pH of 7.5 with concentrated sulfuric acid and passed through a column packed with about 500 ml of granular active carbon to remove the impurities. Elution is carried out with about 1 l of water and then with about 2 l of 0.5N sulfuric acid, whereby most of the active substances are eluted out in a fairly pure form. The active fractions obtained by elution with 0.5N sulfuric acid are neutralized with an anion exchange resin, Dowex 44 ($OH^-$ form) and mixed with the active fractions obtained by elution with water. The mixture is then concentrated under reduced pressure, whereby a crude powder containing the XK-88 series, is obtained. The total activity of the thus obtained powder corresponds to that of about 3 g of the sulfate of XK-88-5.

EXAMPLE 3

In this example, the crude powder containing XK-88-1, XK-88-2, XK-88-3, and XK-88-5 obtained in Example 2 is dissolved in about 3 l of water and adjusted to a pH of 8.0 with concentrated sulfuric acid. The solution is then passed through a column packed with about 500 ml of a cation exchange resin, Amberlite CG-50 ($NH_4^+$ form). After washing the column with water, elution is carried out with 4.5 l of 0.2N aqueous ammonia and then with 0.5N aqueous ammonia, at a rate of about 1 l/hour. The eluate is collected in fractions of 20 ml each. Using 0.2N aqueous ammonia, XK-88-1 and a mixture of XK-88-3 and XK-88-5 are eluted in fractions Nos. 50–165 and in fractions Nos. 166–230, respectively. Thereafter using 0.5N aqueous ammonia XK-88-2 is eluted out.

Active components contained in each fraction are confirmed by silica gel thin layer chromatography. Development is carried out at room temperature for 3–4 hours using developer II (10% ammonium acetate : methanol = 1:1) and developer M (n-butanol : ethanol : chloroform : 17% aqueous ammonia = 4:5:2:5). The components are detected by such color reactions as ninhydrin reaction and Rydon-Smith reaction. Activity of the components is determined by bioautography using an agar plate of *Bacillus subtilis* No. 10707. With developer II, XK-88-1, XK-88-2, XK-88-3, and XK-88-5 show Rf values of 0.58, 0.45, 0.39 and 0.20, respectively and with developer M, XK-88-1, XK-88-2, XK-88-3, and XK-88-5 show Rf values of 0.31, 0.38, 0.27, and 0.50, respectively.

The active fractions are then respectively concentrated under reduced pressure to remove ammonia. As a result, a concentrate containing XK-88-1, a concentrate containing XK-88-2, and a concentrate containing XK-88-3 and XK-88-5 are obtained. The yield of the active substances contained in each concentrate corresponds to about 250 mg, 200 mg, and 1.5 g of the sulfate of XK-88-5, respectively.

EXAMPLE 4

In this example, the active fraction containing XK-88-1 as a main component, which is obtained in Example 3, is concentrated. The concentrate is dissolved in about 50 ml of 50% methanol and the solution is passed through a column packed with about 200 ml of silica gel previously treated with 50% methanol. XK-88-1 is first eluted out with 50% methanol. Thereafter contaminating traces of XK-88-3 and XK-88-5 are eluted out with 50% methanol containing 5% ammonium acetate. After it is confirmed by silica gel thin layer chromatography using developer II and developer M that the fraction first obtained contains a single component, XK-88-1, the fraction is concentrated under reduced pressure to remove methanol. The concentrate is adjusted to a pH of 7.5 with 6N sulfuric acid and passed through a column (about 200 ml) packed with Amberlite CG-50 ($NH_4^+$ form). After washing the column with water, elution is carried out with about 1 l of 0.2N aqueous ammonia. To remove ammonia the active fraction is concentrated to about 50 ml under reduced pressure. Further, the concentrate is adjusted to a pH of 4.5 with 6N sulfuric acid and about 200 volumes of methanol is added dropwise thereto with stirring, whereby a white precipitate is formed. The precipitate is separated by filtration and washed with methanol. After drying, about 12 g of a purified preparate of the sulfate of XK-88-1 is obtained.

EXAMPLE 5

In this example, the active fraction containing XK-88-1 as a main component, which is obtained in Example 3, is concentrated to about 50 ml under reduced pressure. Then 250 ml of methanol is added thereto and the mixture is stirred for 15 minutes. After the mixture is allowed to stand at 0°C overnight, a precipitate is formed. The precipitate is separated with a glass filter. Since the precipitate is poorly soluble in methanol, it is washed with methanol. After washing, the precipitate is suspended in about 500 ml of methanol and dissolved with heating. The solution is then subjected to filtration and the filtrate is concentrated under reduced pressure. As a result, a crystalline precipitate is formed. After the concentrate is allowed to stand at 0°C, additional crystalline precipitate is formed. The precipitate is separated by filtration. Recrystallization is repeatedly carried out from methanol. The thus obtained colorless crystals are separated by filtration and washed with methanol. After drying the resulting crystals under reduced pressure, about 7 g of XK-88-1 (free base) is obtained.

EXAMPLE 6

In this example, the active fraction containing XK-88-2 as a main component, which is obtained in Example 3, is concentrated under reduced pressure and an equal amount of methanol is added thereto. The mixture is passed through a column packed with about 200 ml of silica gel previously treated with 50% methanol. After washing the column with about 1 l of 50% methanol, development is carried out with 50% methanol containing 5% ammonium acetate. XK-88-2 which exhibits Rf values of 0.45 and 0.38 in silica gel thin layer chromatography using developer II and developer M, respectively, is first eluted. Then, contaminating traces of XK-88-3 and XK-88-5 are eluted. By silica gel thin layer chromatography, it is confirmed that the first fraction obtained contains XK-88-2. The active fraction containing XK-88-2 is concentrated to remove methanol. The concentrate is then passed through a column packed with 100 ml of Amberlite CG-50 ($NH_4^+$ form) for de-salting. After washing the column with water, elution is carried out with 0.5N aqueous ammonia. The active fraction is concentrated and passed through a column packed with about 300 ml of silica gel. Development is carried out with a solvent comprising n-butanol, ethanol, chloroform and 17% aqueous ammonia (4:5:2:5). The eluted active fraction is concentrated to remove organic solvents and ammonia. The concentrate is then passed through a column packed with about 100 ml of Amberlite CG-50 ($NH_4^+$ form). After washing the column with water, elution is carried out with 0.5N aqueous ammonia. The active fraction is concentrated to about 3 ml under reduced pressure to remove ammonia. The concentrate is then dissolved in about 100 ml of methanol and the solution is adjusted to a pH of 4.5 with 6N sulfuric acid. As a result, a white precipitate is formed which is separated by filtration and washed with methanol. After drying the precipitate under reduced pressure, about 250 mg of a purified preparate of the sulfate of XK-88-2 is obtained.

EXAMPLE 7

In this example, the mixture containing XK-88-3 and XK-88-5 which is obtained in example 3 is concentrated to about 10 ml. The concentrate is passed through a column packed with about 500 ml of silica gel. Development is carried out with a solvent comprising n-butanol, ethanol, chloroform and 17% aqueous ammonia (4:5:2:5). The eluate is collected in fractions of 20 ml each. XK-88-5 and XK-88-3 are eluted in fractions Nos. 95–121 and in fractions Nos. 133–158, respectively. XK-88-3 contained in the latter fractions exhibits Rf values of 0.39 and 0.27 by silica gel thin layer chromatography using developer II and developer M, respectively. XK-88-5 contained in the former fractions exhibits Rf values of 0.25 and 0.50 in silica gel thin layer chromatography using developer II and developer M, respectively. After confirming the active component contained in each fraction according to the above Rf values, the fractions containing the same components are combined.

EXAMPLE 8

In this example, the active fraction containing XK-88-3 as a main component which is obtained in Example 7 is dried under reduced pressure to remove organic solvents and ammonia. The resulting dry matter is dissolved in 50% methanol and passed through a column packed with 50 ml of silica gel. The column is then washed with 50% methanol to remove any contaminating traces of XK-88-1. XK-88-3 is then eluted out with 50% methanol containing 5% ammonium acetate. The active fractions are combined and concentrated under reduced pressure to remove methanol. The concentrate is then passed through a column packed with about 50 ml of Amberlite CG-50 ($NH_4^+$ form), and, after washing the column with water to remove ammonium acetate, elution is carried out with 0.5N aqueous ammonia to obtain active fractions. The active fractions are combined and concentrated to about 3 ml to remove ammonia. The concentrate is adjusted to a pH of 4.5 with 6N sulfuric acid and added dropwise to about 100 ml of ethanol whereby a white precipitate is formed. The precipitate is then separated by filtration, washed with ethanol and dried under reduced pressure, whereby about 60 mg of a purified preparate of the sulfate of XK-88-3 is obtained.

EXAMPLE 9

In this example, the active fraction containing XK-88-5 as a main component which is obtained in Example 7 is concentrated under reduced pressure. The concentrate is dissolved in an excess amount of methanol and adjusted to a pH of 4.5 with 6N sulfuric acid, whereby a crude powder of the sulfate of XK-88-5 is precipitated. The precipitate is separated by filtration, washed with methanol and dried under reduced pressure, whereby about 600 mg of a crude powder of the sulfate of XK-88-5 is obtained. The thus obtained crude powder is suspended in a solvent comprising n-butanol, ethanol, chloroform and concentrated aqueous ammonia (4:5:2:4). The suspension is passed through a column packed with about 500 ml of silica gel and development is carried out with the same solvent. Active components contained in the eluted fractions are examined by reference to the Rf values by silica gel thin layer chromatography. The fractions containing only XK-88-5 are combined and concentrated under reduced pressure to remove organic solvents and ammonia. Thereafter, the concentrate is passed through a column packed with 200 ml of Amberlite CG-50 ($NH_4^+$ form). After washing the column with water, elution is carried out with 0.5N aqueous ammonia. The active fraction is concentrated to about 10 ml under reduced pressure to remove ammonia. The concentrate is then dissolved in about 200 ml of methanol and adjusted to a pH of 4.5 with 6N sulfuric acid, whereby a white precipitate is formed. The precipitate is separated by filtration and washed with methanol. The solution of methanol containing the precipitate is dried under reduced pressure, whereby about 400 mg of a purified preparate of the sulfate of XK-88-5 is obtained.

What is claimed is:
1. A method for producing antibiotic compounds of the formula

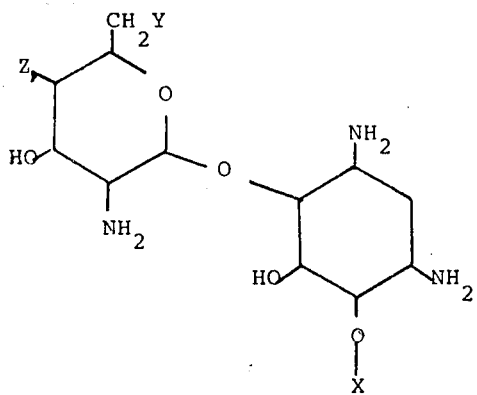

wherein X represents

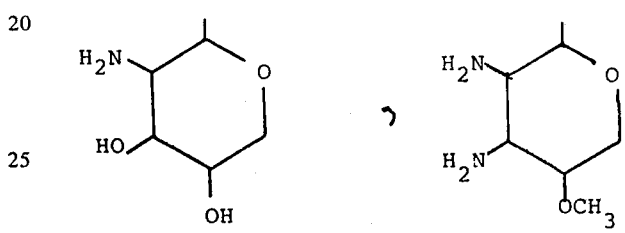

or —H; Y represents —$NH_2$ or —OH, and is —$NH_2$ when X is —H; and Z represents —H or —OH and is —H when X is —H, which comprises culturing *Streptomyces hofuensis* ATCC 21970, or a mutant thereof capable of producing at least one of said compounds, in a nutrient medium containing assimilable sources of nitrogen and carbon until substantial antibacterial activity is imparted to said medium and isolating at least one of said compounds therefrom.

2. A process according to claim 1 wherein the antibiotic compound of the formula is isolated from said culture medium.

3. A process according to claim 1 wherein the antibiotic compound of the formula

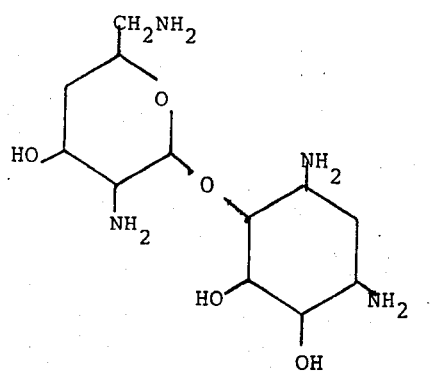

is isolated from said culture medium.

4. A process according to claim 1 wherein the antibiotic compound of the formula

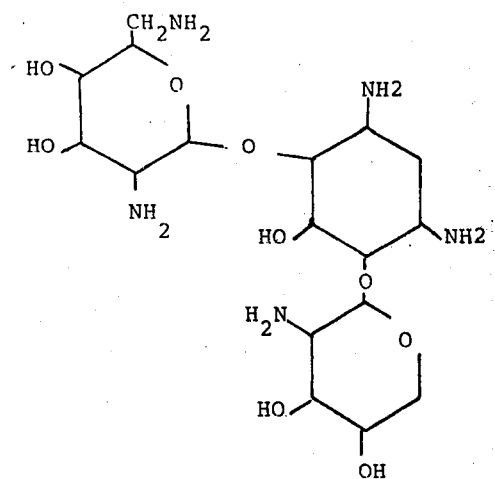

is isolated from said culture medium.

5. A process according to claim 1 wherein the antibiotic compound of the formula

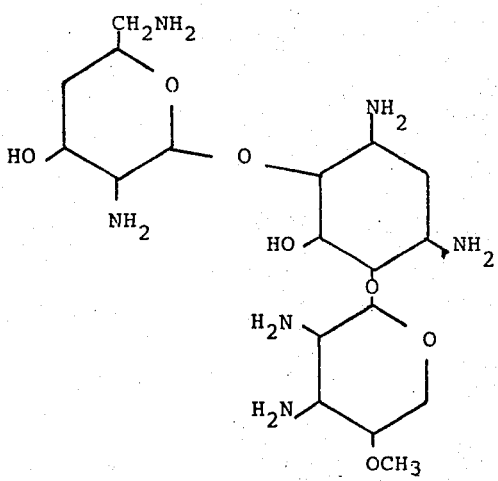

is isolated from said culture medium.

6. A process according to claim 1 wherein said culturing step is continued for 2 to 15 days.

7. A process according to claim 1 wherein said culturing step is carried out at from 26°C. to 43°C. and at about neutral pH.

* * * * *

UNITED STATES PATENT OFFICE
CERTIFICATE OF CORRECTION

Patent No. 3,939,043            Dated February 17, 1976

Inventor(s) TAKASHI NARA, et al.

It is certified that error appears in the above-identified patent and that said Letters Patent are hereby corrected as shown below:

Col. 1, line 53, "sulfate" should be --free base--;

Col. 1, lines 54 and 55, "free base" should be --sulfate--.

Signed and Sealed this fifteenth Day of June 1976

[SEAL]

Attest:

RUTH C. MASON
Attesting Officer

C. MARSHALL DANN
Commissioner of Patents and Trademarks